United States Patent [19]

Koenig et al.

[11] 4,411,752

[45] Oct. 25, 1983

[54] PREPARATION OF 1-MONOCHLOROETHYLCARBAMYL CHLORIDE

[75] Inventors: Karl-Heinz Koenig, Frankenthal; Karl-Heinz Feuerherd, Ludwigshafen, both of Fed. Rep. of Germany

[73] Assignee: BASF Aktiengesellschaft, Fed. Rep. of Germany

[21] Appl. No.: 247,984

[22] Filed: Mar. 26, 1981

[30] Foreign Application Priority Data

Apr. 5, 1980 [DE] Fed. Rep. of Germany ....... 3013270

[51] Int. Cl.$^3$ ............................................. B01J 19/12
[52] U.S. Cl. ............................................. 204/158 HA
[58] Field of Search ........................ 204/158, 158 HA

[56] References Cited

U.S. PATENT DOCUMENTS 3,535,360  10/1970  Holtschmidt et al. ...... 204/158 HA

FOREIGN PATENT DOCUMENTS 2732284  2/1979  Fed. Rep. of Germany .
2741980  4/1979  Fed. Rep. of Germany .
1418666  11/1968  Fed. Rep. of Germany .

OTHER PUBLICATIONS

Ullmanns Encyklopädie der technischen Chemie, vol. 9, pp. 11, 12 and 404.
Ullmanns Encyklopädie der technischen Chemie, vol. 17, p. 404.
J. Org. Chem. 26 (1961), pp. 770–779.
J. of Coatings Techn. 49 (1977), pp. 82–86.
Synthesis (1980), pp. 85–110.
Angew. Chem., 74 (1962) pp. 848–855.
Chem. High Polymers (Tokyo)) 13 (1956), p. 390.
J. Polymer Sci. 35 (1959), pp. 215–218.

*Primary Examiner*—Howard S. Williams
*Attorney, Agent, or Firm*—Keil & Witherspoon

[57] ABSTRACT

A process for the preparation of 1-monochloroethylcarbamyl chloride by chlorinating ethyl isocyanate or ethylcarbamyl chloride. The 1-chloroethylcarbamyl chloride obtainable according to the invention is an important starting material for the preparation of 1-chloroethyl isocyanate and vinyl isocyanate and accordingly a valuable starting material for the preparation of pest control agents, dyes, drugs, textile waterproofing agents, detergents, plastics, bleaching agents and adhesives, since the said isocyanates contain, in addition to a reactive isocyanate group, an activated double bond or an activated α-carbon atom.

9 Claims, No Drawings

PREPARATION OF 1-MONOCHLOROETHYLCARBAMYL CHLORIDE

The present invention relates to a process for the preparation of 1-monochloroethylcarbamyl chloride by chlorinating ethyl isocyanate or ethylcarbamyl chloride at from −78° to 0° C., under pressure exposure to light.

The synthesis of 1-monochloroethylcarbamyl choride has hitherto mainly been carried out by the process described in German Laid-Open Application DOS No. 2,741,980, namely by reaction of N-vinyl-N-tert.-butylcarbamyl chloride with hydrogen chloride, and by the process described in German Laid-Open Application DOS No. 2,732,284, namely by reaction of vinyl isocyanate with hydrogen chloride. These processes are expensive since the starting materials are difficult to prepare.

German Laid-Open Application DOS No. 1,418,666 discloses that in the presence of chlorine, under exposure to ultraviolet, 2-chloroethyl isocyanate is converted to the extent of 21% into dichloroethyl isocyanate and to the extent of 37.2% into trichloroethyl isocyanate (Example 2). If sulfuryl chloride is used as the chlorine donor, a 94% yield of trichloroethyl isocyanate, containing only about 10% of carbamyl chloride, is obtained. The only carbamyl chloride formed is trichloroethylcarbamyl chloride.

German Pat. No. 1,122,058 describes a process for the preparation of 1-haloalkyl isocyanates from alkyl isocyanates or alkylcarbamyl halides by reaction with halogenating agents. However, this process gives substantial proportions of polymers. In all examples it is not ethyl isocyanate, but β-chloroethyl isocyanate which is used, and the chlorination, at 80°–150° C., under exposure to ultraviolet, gives mixtures of β-chloroethyl, α,β-dichloroethyl, β,β-dichloroethyl, the isomeric trichloroethyl, the isomeric tetrachloroethyl and pentachloroethyl isocyanates. The publication emphasizes that the reaction of alkyl isocyanates with halogenating agents smoothly gives the halogenated isocyanates; there is no mention of the formation of halogenated carbamyl chlorides. It is emphasized that the reaction is to be carried out at not below ambient temperature, and can advantageously also be carried out at elevated temperatures, under exposure to light or using halogen transfer agents, eg. iron-III chloride.

Angew. Chem., 74 (1962), 848–855 discloses that alkylcarbamyl chlorides can be reacted with elementary chlorine to give the corresponding α-chloroalkylcarbamyl chlorides. However, the resulting products are mixtures, both in respect of the degree of halogenation and in respect of the position of the halogen atoms which enter the molecule. The process is unsatisfactory in respect of yield and purity of the end product, and is insufficiently simple and economical. The process is regarded as so unfavorable that German Laid-Open Application DOS No. 2,732,284 abandons direct chlorination and recommends the above reaction with hydrogen halide, because it alleges that only in this way are α-haloethylcarbamyl halides obtainable more simply and more economically, in better yield and higher purity, and with simpler working up, since the method does not give a mixture of numerous components.

Synthesis (1980), 85–110 states explicitly (page 90) that the chlorination of alkyl isocyanates, with heating, for example at 55°–60° C., and under exposure to ultraviolet, gives α-chloroalkyl isocyanates. It makes no mention of the formation of corresponding carbamyl chlorides. As shown by the Examples in Table 7, more highly chlorinated or perchlorinated isocyanates, or corresponding mixtures, are obtained when using alkyl isocyanates. Whilst both methyl isocyanate and benzyl isocyanate free from halogen substituents are used, this investigation again does not employ halogen-free or α-halogenated ethyl isocyanates, but always uses β-halogenated, in particular β-perhalogenated, ethyl isocyanates.

We have found that 1-monochloroethylcarbamyl chloride is obtained in an advantageous manner by reacting an isocyanate or ethylcarbamyl chloride with a halogenating agent if ethyl isocyanate or ethylcarbamyl chloride is reacted with chlorine at from −78° to 0° C., under exposure to light.

Further, we have found that the process proceeds advantageously if an excess of free chlorine not exceeding 0.1 mole per mole of ethyl isocyanate is used in the reaction.

The reaction can be represented by the following equation:

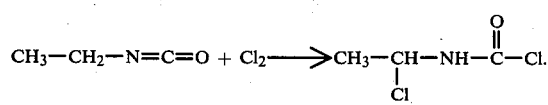

Compared to the prior art, the process according to the invention surprisingly gives 1-monochloroethylcarbamyl chloride selectively, in high yield and high purity, by a simpler and more economical method. Halogenating agents which are more difficult to obtain, such as sulfuryl chloride, are not needed. Both the chlorine used as the halogenating agent, and the ethyl isocyanate employed, are easily obtainable. Expensive purification operations and working-up operations are saved, since the reaction does not give a heterogeneous mixture of components of differing degrees of halogenation. All these advantageous results achieved with the process according to the invention are surprising. In view of the prior art, it would have been expected that under the conditions according to the invention isocyanates, and not carbamyl chlorides, would have been the end products. It is also surprising that chlorinated- and, moreover, 1-monochlorinated-ethylcarbamyl chloride is produced as the principal end product, in such high purity. Furthermore, German Pat. No. 1,122,058 (Example 1) shows that on chlorination under exposure to light, at 40°–70° C., chloromethyl isocyanate is obtained from methylcarbamyl chloride, ie. the converse reaction does not take place; it is true that chloromethylcarbamyl chloride forms in the receiver, but this is produced from the chloromethyl isocyanate, ie. the compound which has already undergone chlorination, and hydrogen chloride.

In particular, it was to be expected that under the conditions according to the invention, not only would isocyanates principally be formed, but heterogeneous mixtures would be obtained. In view of Example 6 of German Pat. 1,122,058 mixtures of 2 monochloroethyl isocyanates, 3 dichloroethyl isocyanates, 3 trichloroethyl isocyanates, 2 tetrachloroethyl isocyanates and one pentachloroethyl isocyanate were to be expected, without Example 6 being able to give any indication of their ratios, since the use of β-chloroethyl isocyanate in Example 6 to a certain extent dictated the direction in which the reaction proceeded. Therefore, even on detailed consideration, the most that might have been expected speculatively was a light formation of carbamyl chlorides, but this would under all circumstances have been expected to be accompanied by a further 11 different carbamyl chloride components as reaction products.

It also had to be regarded as dubious whether α-monochloroethyl isocyanate was at all clearly obtainable by chlorinating ethyl isocyanate, since no example of this is to be found in the prior art and in every case only β-substituted ethyl isocyanates, for example trichloro compounds or β-chloro compounds, are used. However, even in that case, β-monochloroethyl isocyanate only gives a mixture of products and does not give pure α,β-dichloroethyl isocyanate. Overall, therefore, the formation of pure α,β-dichloroethyl isocyanate, and even more so the formation of α-monochloroethylcarbamyl chloride, under the conditions according to the invention had to be ruled out as a possibility.

The starting material used can be prepared, for example, by the processes described in Ullmanns Encyklopädie der technischen Chemie, volume 13 (4th edition, 1977), 350–354. The chlorine is used in the stoichiometric amount or in a lesser or greater amount than this, preferably in an amount of from 0.1 to 1.5, especially from 0.5 to 1.1, moles of chlorine per mole of ethyl isocyanate. The reaction is carried out at from −78° C. to 0° C., advantageously from −75° to 0° C., especially from −40° to −10° C., under atmospheric or superatmospheric pressure, preferably at from 0.3 to 5, especially from 0.7 to 2, bar, continuously or batchwise. It can be carried out without a solvent, but is advantageously carried out in a solvent which, because of its relatively low melting point, is suitable for use at the chosen chlorination temperature, and is insert toward ethyl isocyanate under the reaction conditions. Water is not employed. Preferably, the reaction is carried out in a solvent which can be used as the reaction medium for the further conversion of the end product. Examples of suitable solvents (with melting points given in parentheses) are: halohydrocarbons, eg. methylene chloride (−96° C.), chloroform (−63.5° C.), carbon tetrachloride (−22.9° C.), trichloroethylene (−83° C.), tert.-butyl chloride (−28.5° C.), 1,2-dichloroethane (−35.5° C.), 1,2-dibromopropane (−55° C.), 1,2-dichloropropane (−100° C.), 1,4-dibromobutane (−20° C.), chlorobenzene (−45° C.) and 1-chloronaphthalene (−17° C.); esters, eg. methyl acetate (−98° C.), ethyl acetate (−83.6° C.) and nitromethane (−29.2° C.); aromatic hydrocarbons, eg. o-xylene (−27.9° C.), m-xylene (−49.3° C.) and tert.-butylbenzene (−60.9° C.); carbon disulfide (−112° C.); and corresponding mixtures. The solvent is advantageously used in an amount of from 200 to 10,000 percent by weight, preferably from 300 to 2,000 percent by weight, based on ethyl isocyanate.

The reaction is carried out under exposure to light, as a rule ultraviolet, advantageously of wavelengths from 200 to 700 nanometers, preferably from 200 to 400 nanometers. The ultraviolet source used can be any source with strong emission in the ultraviolet region, for example a carbon arc lamp, mercury vapor lamp, fluorescent lamp, argon incandescent lamps or xenon lamps. The light source should advantageously be a broad light source, where necessary employing reflectors. As a rule, the exposure time is from 30 to 360, preferably from 120 to 300, minutes. As regards the method of exposure and the light sources, reference may be made to Ullmanns Encyklopädie der technischen Chemie, volume I, pages 762 et seq. Advantageously, the exposure employed is from 0.2 to 10,000 Watt hours, preferably from 20 to 1,000 Watt hours, especially from 100 to 500 Watt hours, of light per kilogram of starting material. It is also possible to introduce the light source into the reaction space, for example by employing an immersed lamp. The reaction mixture can advantageously be irradiated in a continuous flow reactor or, when employing a discontinuous method, in individual batches. A further suitable method is to mix the contents of the reactor by thorough circulation, for example by circulating a part-stream through an external circuit which can at the same time be used to control the temperature of the reaction mixture. The process can be carried out continuously, with the photoreactors operated in series or in parallel. Falling film photoreactors, which allow the starting compound to be reacted under exposure to light, as a gas-liquid reaction, in a non-stationary thin layer of liquid, are particularly advantageous; in this context, reference may be made to Angew. Chem. 86 (1974), 706–707, and Tetrahedron Letters (1976), 4,057–4,060.

The reaction may in detail be carried out as follows: a mixture of chlorine, the starting material and the solvent is chlorinated, with thorough mixing, at the reaction temperature, for the stated reaction time, whilst being exposed to an ultraviolet source. Where appropriate, the reaction mixture can, toward the end of the reaction, be exposed to ultraviolet without additional supply of chlorine, for example for the last 10–90 minutes of the reaction, or be supplied with additional chlorine without exposure to light, for example for the last 10–60 minutes of the reaction. Such final reactions, in which either the light exposure or the supply of chlorine is stopped, advantageously account for from 0 to one-quarter of the total reaction time.

If the chlorination is carried out without a solvent, it is advantageous to confine the reaction to a partial conversion so that the 1-monochloroethylcarbamyl chloride formed does not precipitate as a solid under the prevailing concentration conditions and temperature conditions. Preferably, the conversion is 15–50 percent.

Advantageously, immediate reaction of the chlorine passed into the reaction mixture is ensured by circulating and irradiating in a non-stationary thin layer, with continuous cooling. After the reaction, the end product can be separated off in a conventional manner, for example by crystallization and filtration, and be converted further. It is, however, also possible to convert the crude reaction mixture further without isolating the end product according to the invention.

To achieve a high yield and high purity of 1-chloroethylcarbamyl chloride, it is advantageous only to introduce as much chlorine per unit time as will react with the ethyl isocyanate in the same unit time. The excess of free chlorine should not exceed 0.1 mole, preferably 0.05 mole, per mole of ethyl isocyanate in the reaction mixture.

In a preferred embodiment, the reaction mixture is not subjected to fractional distillation; instead, the solvent is first removed, advantageously by distillation under reduced pressure and/or below 30° C., and the residue is recrystallized, for example from methylene chloride, chloroform, carbon tetrachloride, n-pentane, n-hexane, diethyl ether, methyl tert.-butyl ether, 1,2-dichloroethane, 1,1,1-trichloroethane or 1,1,2-trichloroethane, the end product thereby being obtained in a pure form. Another preferred embodiment is to cool the reaction mixture and filter off the end product which precipitates. Advantageously, the temperature at which the reaction mixture is worked up should not exceed +30° C., preferably +10° C., more especially −10° C.

The 1-chloroethylcarbamyl chloride obtainable according to the invention is a valuable starting material for the preparation of 1-chloroethyl isocyanate (Ia) and vinyl isocyanate (Ib). For example, it can be converted, at from −10° to +150° C., in the presence of α-pinene, advantageously from 2 to 20 moles of α-pinene per mole of end product, with a reaction time of 0.5–6 hours, to a mixture of 1-chloroethyl isocyanate Ia and vinyl isocyanate Ib, which can be further converted as a mixture; the end products Ia and Ib can, however, also be isolated from the reaction mixture, advantageously directly after the reaction, by increasing the temperature and carrying out a fractional distillation.

It is also possible to react the 1-monochloroethylcarbamyl chloride of the formula

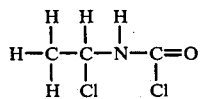                                II (a1) with a halogen-free isocyanate of the formula

R$^1$—N=C=O                                      III where R$^1$ is alkyl, cycloalkyl, aryl, aralkyl or alkylaryl, and/or (a2) with a diisocyanate of the formula

O=C=N—R$^2$—N=C=O                                IV where R$^2$ is alkylene, cycloalkylene, arylene, alkylarylene or arylalkylene, or (a3) with vinyl isocyanate Ib, to give a mixture of 1-monochloroethyl isocyanate of the formula

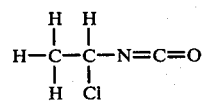                                Ia and vinyl isocyanate of the formula

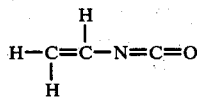                                Ib

Where 1-chloroethylcarbamyl chloride, hexamethylene diisocyanate and vinyl isocyanate are used, the reaction can be represented by the following equations:

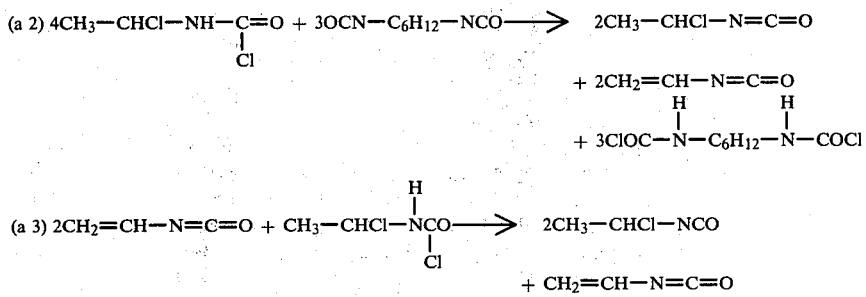

The starting materials II and III (reaction a1) or the starting materials II and IV (a2) or the compounds Ib and II (a3) can, in each case, be reacted in stoichiometric amounts or using an excess of either component; advantageously, the amounts used are, in process (a1), from 15 to 25 moles of compound III per mole of compound II, in the case of process (a2) from 3 to 14 moles of compound IV per mole of compound II, and in the case of process (a3) from 0.5 to 1 mole of compound II per mole of compound Ib. In general, reaction (a1) according to the invention gives mixtures of from 0.05 to 0.2 mole of end product Ia per mole of end product Ib or, when using the above advantageous amounts of starting materials, from 0.05 to 0.1 mole of end product Ia per mole of end product Ib; reaction (a2) gives mixtures of from 0.2 to 0.7 mole of end product Ia per mole of end product Ib, or from 0.3 to 0.6 mole of end product Ia per mole of end product Ib when using the above advantageous amounts of starting materials; reaction (a3) gives mixtures of from 2 to 20 moles of end product Ia per mole of end product Ib, or from 7 to 20 moles of end product Ia per mole of end product Ib when using the above advantageous amounts of starting materials. The higher the concentration of compound III in (a1), IV in (a2) and II in (a3) is in comparison to the other starting materials in each case, the greater becomes the proportion of end product Ib in the mixture in the case of process (a1) and of process (a2), and of Ia in the mixture in the case of process (a3). Accordingly, by a suitable experiment it is easy to establish, for each process, how to obtain a desired ratio of end products Ia and Ib, or how to obtain substantially only one component in the end product mixture. In the case of process (a3), substantially only end product (Ia) is obtained, whilst in the case of process (a1) and (a2) substantially only end product Ib is obtained.

Preferred starting materials III and IV and accordingly preferred end products Ia and Ib are those where R$^1$ is alkyl of 1 to 12, especially of 1 to 6, carbon atoms, cyclohexyl, aralkyl or alkylaryl of 7 to 12 carbon atoms, or phenyl, and R$^2$ is alkylene of 1 to 12 carbon atoms, especially of 1 to 6 carbon atoms, cyclohexylene, aralkylene or alkylarylene of 7 to 12 carbon atoms, or phenylene. Cycloalkyl R$^1$ or cycloalkylene R$^2$ can advantageously be a monocyclic or bicyclic radical which is unsubstituted or substituted by alkyl of 1 to 3 carbon atoms; in the case of a bicyclic radical, the two cycloalkyl nuclei can be fused or can be linked direct or via a methylene group; in the case of starting materials IV, the two isocyanato groups can (1) both be located on one cycloalkyl nucleus or (2) both be located on one of the two cycloalkyl nuclei or (3) be located so that there is one on each of the two cycloalkyl radicals or (4) be bonded, in the case of one or both of the isocyanato groups, to one or both of the cycloalkyl nuclei via alkylene groups of 1 to 3 carbon atoms. The end product Ib isolated from the mixture, for example by distillation, after the reaction can, in process (a3), be re-used for the reaction, so as to achieve a high temperature of one or other end product. If desired, starting material II can also be reacted with a mixture of starting materials III and IV and vinyl isocyanate Ib.

Examples of suitable starting materials III are ethyl isocyanate, propyl isocyanate, isopropyl isocyanate, butyl isocyanate, isobutyl isocyanate, sec.-butyl isocyanate, tert.-butyl isocyanate, pentyl isocyanate, 3-methylbutyl isocyanate, hexyl isocyanate, 2-ethylhexyl isocyanate, cyclohexyl isocyanate, phenyl isocyanate, benzyl isocyanate, 3-methylphenyl isocyanate and α-naphthyl isocyanate.

Examples of suitable starting materials IV are hexamethylene diisocyanate, toluylene diisocyanate, bis-(3-methyl-4-isocyanato-cyclohexyl)-methane, 1,1,4,4-tetramethylbutane 1,4-diisocyanate, 1,1,6,6-tetramethylhexane, 1,6-diisocyanate and 3-isocyanatomethyl-3,5,5-trimethylcyclohexyl isocyanate.

An advantageous method of choosing the starting materials III and IV is in relation to the boiling point of the 1,2-unsaturated isocyanate Ib which is expected from the reaction according to the invention. The boiling point of this isocyanate should be slightly or, preferably, significantly lower, advantageously 10°–100° C. lower, than that of the starting materials III and IV. Equally, the boiling point of the 1-chloroethyl isocyanate should be considerably lower, advantageously from 10° to 50° C. lower, than that of the starting materials II, III and IV. Alternatively, on distilling off a mixture of two or three components, for example the isocyanates Ia, Ib and III, the proportion of end product Ia can be virtually completely converted to the desired isocyanate Ib by renewed distillation of the starting material III. The preferred method of carrying out the process according to the invention is to remove the desired mixture, or one of the end products, preferably end product Ib, immediately and continuously from the equilibrium by means of a stream of inert gas under atmospheric pressure, especially in the case of low-boiling reaction products, or to carry out the reaction under reduced pressure, or to combine the use of a stream of inert gas with working under reduced pressure, amongst which alternatives, however, the use of solely a stream of inert gas, for example of dry nitrogen or dry air, is preferred.

If, in a case where procedure (a1) or (a2) is used, sharp separation of the isocyanate Ib cannot be achieved after a single reaction of the 1-chloroethylcarbamyl chloride II, the crude end product mixture discharged with the carrier gas stream can advantageously be reacted again with starting material III or IV, to give the desired 1,2-unsaturated isocyanate. The reaction residue, which consists predominantly of carbamyl chloride corresponding to starting material III or IV, can be used in a conventional manner to regenerate the isocyanate, for example by thermal elimination of hydrogen chloride and subsequent distillation of the crude isocyanate, the hydrogen chloride liberated being used elsewhere for the preparation of, for example, aqueous hydrochloric acid, ie. the entire hydrogen halide eliminated can be economically reused and recycled.

The higher the reaction temperature and the longer the reaction time, the higher is the proportion of end product Ib in the final mixture. The reaction is as a rule carried out at from 0° to 150° C., advantageously from 0° to 50° C. in the case of the preparation of mixtures containing more than 1.5, in particular from 1.5 to 20, moles of end product Ia per mole of end product Ib, advantageously from 40° to 70° C. in the case of the preparation of mixtures containing from 0.5 to 1.5, especially from 0.9 to 1.1, moles of end product Ia per mole of Ib, and advantageously from 70° to 120° C. in the case of the preparation of mixtures containing less than 0.5, in particular from 0.05 to less than 0.5, mole of end product Ia per mole of end product Ib, in each case under atmospheric or superatmospheric pressure, continuously or batchwise. Advantageously, the reaction is started at from 0° to 30° C., the temperature is raised slowly and the reaction is completed at the advantageous reaction temperatures mentioned above. The reaction time is in general 0.1–5 hours, advantageously from 2 to 4 hours in the case of the preparation of mixtures containing more than 1.5, in particular from 1.5 to 20, moles of end product Ia per mole of end product Ib, from 0.5 to 3 hours in the case of the preparation of mixtures containing from 0.5 to 1.5, especially from 0.9 to 1.1, moles of end product Ia per mole of end product Ib, and from 1.5 to 3 hours in the case of the preparation of mixtures containing less than 0.5, in particular from 0.05 to less than 0.5, mole of end product Ia per mole of end product Ib.

Preferably, the reaction is carried out in the absence of added solvent, but solvents which are inert under the reaction conditions can be used. Examples of suitable solvents are aromatic hydrocarbons, eg. toluene, ethylbenzene, o-, m- and p-xylene, isopropylbenzene and methylnaphthalene, halohydrocarbons, especially chlorohydrocarbons, eg. tetrachloroethylene, 1,1,2,2- and 1,1,1,2-tetrachloroethane, dichloropropane, methylene chloride, dichlorobutane, isopropyl bromide, n-propyl bromide, butyl bromide, chloroform, ethyl iodide, propyl iodide, carbon tetrachloride, 1,1,1- and 1,1,2-trichloroethane and trichloroethylene, aliphatic and cycloaliphatic hydrocarbons, eg. heptane, nonane, gasoline fractions boiling within a range of from 70° to 190° C., cyclohexane, methylcyclohexane, decalin, petroleum ether, hexane, naphtha, 2,2,4-trimethylpentane, 2,2,3-trimethylpentane, 2,3,3-trimethylpentane and octane, and corresponding mixtures. The solvent is advantageously used in an amount of from 200 to 10,000 percent by weight, preferably from 300 to 2,000 percent by weight, based on starting material II.

The reaction can be carried out as follows: a mixture of the starting materials is reacted, at the reaction temperature and for the reaction time stated above. The end products Ia and Ib are then isolated from the reaction mixture, advantageously directly during the reaction or after the reaction, by raising the temperature and effecting a fractional distillation.

The vinyl isocyanate Ib and 1-monochloroethyl isocyanate Ia obtainable in this way are valuable starting materials for the preparation of pest control agents, dyes, drugs, textile waterproofing agents, detergents, plastics, bleaching agents and adhesives, since they possess an activated double bond or an activated α-carbon atom in addition to a reactive isocyanate group. Furthermore, vinyl isocyanate is an important monomer, which can in various ways be converted to chain polymers and ladder polymers, for example radiation-hardening surface-coating resins (Chem. High Polymers (Tokyo) 13 (1956), 390; J. Polymer Sci. 35 (1959), 215; J. Org. Chem. 26 (1961),770; J. of Coatings Techn. 49 (1977), 82). The compounds Ia and Ib can be converted to urethanes, for example for use as foams or as very flexible high molecular weight coatings, or can be converted to ureas. Regarding their use, reference may be made to the above publications and to Ullmanns Encyklopädie der technischen Chemie, volume 9, pages 11, 12 and 404, and volume 17, page 204 (3rd edition).

In the Examples which follow, parts are by weight and bear the same relations to parts by volume as that of the kilogram to the liter.

EXAMPLE 1

A mixture of 110 parts of ethyl isocyanate and 440 parts of chlorobenzene is circulated at a rate of 4,000 parts per volume/minute in a falling film photoreactor at −3° C. 110 parts of chlorine are passed in over 4 hours, under irradiation from an ultraviolet lamp. The mixture is then irradiated for a further hour without introducing gas. The excess of chlorine over the entire reaction and post-irradiation time is less than 0.01 mole per mole of unconverted ethyl isocyanate. 173 parts (87.8% of theory) of 1-chloroethylcarbamyl chloride are obtained, the conversion of ethyl isocyanate (determined by gas chromatography) being 89.7%.

EXAMPLE 2

A mixture of 110 parts of ethyl isocyanate and 440 parts of chlorobenzene is circulated at a rate of 10,000 parts per volume/minute in a falling film photoreactor at −10° C. 110 parts of chlorine are passed in over 2.5 hours, under irradiation from an ultraviolet lamp. The excess of chlorine over the entire reaction and post-irradiation time (1 h) is less than 0.05 mole per mole of unconverted ethyl isocyanate. 151 parts (89.4% of theory) of 1-chloroethylcarbamyl chloride are obtained, the conversion of ethyl isocyanate (determined by gas chromatography) being 84.6%.

EXAMPLE 3

A mixture of 110 parts of ethyl isocyanate and 440 parts of chlorobenzene is circulated at a rate of 3,000 parts per volume/minute in a falling film photoreactor at from −15° to −20° C. 80 parts of chlorine are introduced in the course of 5 hours, under irradiation.

Irradiation is then continued for 45 minutes without introducing gas, and thereafter a further 40 parts of chlorine are passed in under irradiation, in the course of 60 minutes. The excess of chlorine over the entire reaction and post-irradiation time is less than 0.1 mole per mole of unconverted ethyl isocyanate. 173.5 parts (98.9% of theory) of 1-chloroethylcarbamyl chloride are obtained, the conversion of ethyl isocyanate (determined by gas chromatography) being 87.8%.

EXAMPLE 4

A mixture of 110 parts of ethyl isocyanate and 440 parts of chlorobenzene is circulated at a rate of 3,500 parts per volume/minute in a falling film photoreactor at from −25° to −30° C. 110 parts of chlorine are passed in over 4 hours, under irradiation from an ultraviolet lamp. The mixture is then irradiated for a further half hour without introducing gas. The excess of chlorine over the entire reaction and post-irradiation time is less than 0.01 mole per mole of unconverted ethyl isocyanate. 172.5 parts (97% of theory) of 1-chloroethylcarbamyl chloride are obtained, the conversion of ethyl isocyanate (determined by gas chromatography) being 89%.

EXAMPLE 5

A mixture of 120 parts of ethyl isocyanate and 720 parts of carbon tetrachloride is circulated at a rate of 4,000 parts per volume/minute in a falling film photoreactor at from −15° to −20° C. 120 parts of chlorine are passed in over 5 hours, under irradiation from an ultraviolet lamp. The mixture is then irradiated for a further hour without introducing gas. The excess of chlorine over the entire reaction and post-irradiation time is less than 0.02 mole per mole of unconverted ethyl isocyanate. The conversion of ethyl isocyanate, determined by gas chromatography, is 86.9%. The solvent is substantially removed under reduced pressure, and after filtration 172.3 parts (82.7% of theory, based on unconverted $C_2H_5NCO$) of 1-chloroethylcarbamyl chloride, of melting point 20° C., are obtained.

EXAMPLE 6 (USE)

A mixture of 142 parts of 1-chloroethylcarbamyl chloride from Example 5, 92.5 parts of tert.-butyl chloride and 426 parts of hexamethylene diisocyanate is heated for 2.5 hours at 40°–78° C. under a pressure of 60 mbar. Distillation gives 89 parts (84.3%) of 1-chloroethyl isocyanate and 1.3 parts (1.9%) of vinyl isocyanate.

EXAMPLE 7

548 parts of ethyl isocyanate are circulated at a rate of 4,000 parts per volume/minute in a falling film photoreactor at from −10° to −15° C. 122 parts of chlorine are passed in over 4 hours, under irradiation with ultraviolet. The excess of chlorine over the entire reaction and post-irradiation time (1 h) is less than 0.01 mole per mole of unconverted ethyl isocyanate. 215.7 parts (88.3% of theory) of 1-chloroethylcarbamyl chloride are obtained, the conversion (determined by gas chromatography) being 19.7%.

EXAMPLE 8 (USE)

The mixture of ethyl isocyanate and 1-chloroethylcarbamyl chloride prepared according to Example 7 is subjected to fractional distillation through a packed column in the course of 3.5 hours, whilst passing dry nitrogen through the column. 48.5 parts (46.2% of theory, based on ethyl isocyanate chlorinated in Example 7) of vinyl isocyanate, of boiling point 38.5° C./1,013 mbar and 331 parts of ethyl isocyanate of boiling point 60° C./1,013 mbar are obtained.

EXAMPLE 9 (USE)

A solution of 57 parts of 1-chloroethylcarbamyl chloride in 100 parts by volume of hexamethylene diisocyanate is introduced slowly at 100° C., in the course of half an hour, under the surface of 572 parts of hexamethylene diisocyanate. At the same time nitrogen is blown through the solution and the exit gas is cooled to −100° C. by means of a cold trap. The reaction mixture is subjected to fractional distillation. 10.2 parts (36.8% of theory) of vinyl isocyanate of boiling point 38.5° C./1,013 mbar and 6.8 parts (16.1% of theory) of 1-chloroethyl isocyanate of boiling point 92° C./1,013 mbar are obtained.

EXAMPLE 10 (USE)

30 parts of 1-chloroethylcarbamyl chloride are dissolved in 100 parts by volume of 1-chloronaphthalene and a solution of 16 parts of vinyl isocyanate in 20 parts by volume of 1-chloronaphthalene is added to the mixture in the course of 0.3 hour at 2° C. 12.5 parts (8% of theory) of vinyl isocyanate and 43 parts (92% of theory) of 1-chloroethyl isocyanate are obtained, the determinations being carried out by gas chromatography.

EXAMPLE 11 (USE)

57 parts of 1-chloroethylcarbamyl chloride are introduced into 700 parts by volume of isopropyl isocyanate at 22° C., the solution is heated to 70° C. in the course of 1.5 hours, whilst passing a slight stream of nitrogen through it, and the reaction product is condensed in a cold trap at −70° C. 12 parts (43% of theory) of vinyl isocyanate, of boiling point 38.5° C./1,013 mbar, and 0.85 part (2% of theory) of chloroethyl isocyanate, of boiling point 92° C/1,013 mbar, are obtained.

EXAMPLE 12 (USE)

57 parts of 1-chloroethylcarbamyl chloride are dissolved in 520 parts of ethyl isocyanate at 22° C. and dry nitrogen is blown through the solution, a Raschig ring column being used in order to achieve a preliminary separation of the 3-component mixture in the column (ie. into ethyl isocyanate, vinyl isocyanate and 1-chloroethyl isocyanate). The reaction mixture is subjected to fractional distillation in the course of 3 hours. 14 parts (50.5% of theory) of vinyl isocyanate of boiling point 38.5° C./1,013 mbar and 466 parts of ethyl isocyanate of boiling point 60° C./1,013 mbar are obtained.

EXAMPLE 13 (USE)

563 parts of 1-chloroethylcarbamyl chloride are dissolved in 2,800 parts by volume of hexamethylene diisocyanate. The solution, totalling 3,100 parts by volume, is introduced in 3 portions (500, 1,500 and 1,100 parts by volume) with different residence times (150, 310 and 225 minutes respectively) into a thin film evaporator operated under atmospheric pressure, with a countercurrent of nitrogen. The jacket temperature is 73°–75° C. and the material passes over at 48°–54° C. The reaction product is collected in a receiver and two downstream cold traps, and the composition is determined by gas chromatography. 145.3 parts (53% of theory) of vinyl isocyanate, of boiling point 38.5° C./1,013 mbar, and 73.8 parts (17.7% of theory) of 1-chloroethyl isocyanate, of boiling point 92° C./1,013 mbar, are obtained.

EXAMPLE 14 (USE)

A mixture of 57 parts of 1-chloroethylcarbamyl chloride, 156 parts of ethyl isocyanate and 841 parts of hexamethylene diisocyante is heated to 90° C. in the course of 3 hours, whilst passing a stream of nitrogen at 22° C. through the mixture. A mixture of 11.8 parts (42.5% of theory) of vinyl isocyanate, of boiling point 38.5° C./1,013 mbar, 10.1 parts (23.8% of theory) of 1-chloroethyl isocyanate of boiling point 92° C./1,013 mbar and 149 parts of ethyl isocyanate is obtained in the distillation receiver.

EXAMPLE 15 (USE)

A mixture of 160 parts of 1-chloroethylcarbamyl chloride and 537 parts of α-pinene is heated from 24° to 105° C. in the course of 2 hours, whilst stirring, and the reaction mixture is subjected to fractional distillation. A total of 27.6 parts (23% of theory) of 1-chloroethyl isocyanate of boiling point 92° C./1,013 mbar and 34.6 parts of vinyl isocyanate of boiling point 38.5° C./1,013 mbar, is obtained.

We claim:
1. A process for producing 1-monochloroethylcarbamyl chloride as the principal product and in high yields which comprises reacting ethyl isocyanate or ethylcarbamyl chloride with chlorine at from −78° to 0° C., under exposure to light.
2. The process of claim 1, wherein, during the reaction, an excess of free chlorine not exceeding 0.1 mole per mole of ethyl isocyanate or ethylcarbamyl chloride is used.
3. The process of claim 1, wherein the reaction is carried out with from 0.1 to 1.5 moles of chlorine per mole of ethyl isocyanate or of ethylcarbamyl chloride.
4. The process of claim 1, wherein the reaction is carried out at from −75° to 0° C.
5. The process of claim 1, wherein the reaction is carried out at from −40° to −10° C.
6. The process of claim 1, wherein the reaction is carried out at from 0.3 to 5 bar.
7. The process of claim 1, wherein the reaction is carried out in a solvent which is used as the reaction medium during the further conversion of the end product.
8. The process of claim 1, wherein the reaction is carried out in a halohydrocarbon, ester, nitromethane, aromatic hydrocarbon, carbon disulfide or corresponding mixtures.
9. The process of claim 1, wherein the reaction is carried out under irradiation with ultraviolet light of wavelength of from 200 to 700 nanometers.

* * * * *